United States Patent
Takai (10) Patent No.: US 9,565,999 B2
(45) Date of Patent: Feb. 14, 2017

(54) OPHTHALMOLOGIC APPARATUS (75) Inventor: Motoya Takai, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 282 days.

(21) Appl. No.: 14/008,511

(22) PCT Filed: Mar. 22, 2012

(86) PCT No.: PCT/JP2012/001969
§ 371 (c)(1),
(2), (4) Date: Sep. 27, 2013

(87) PCT Pub. No.: WO2012/132339
PCT Pub. Date: Oct. 4, 2012

(65) Prior Publication Data
US 2014/0016095 A1   Jan. 16, 2014

(30) Foreign Application Priority Data

Mar. 31, 2011  (JP) ................. 2011-079361

(51) Int. Cl.
A61B 3/14 (2006.01)
A61B 3/00 (2006.01)
A61B 3/10 (2006.01)
A61B 3/12 (2006.01)
A61B 3/15 (2006.01)

(52) U.S. Cl.
CPC ............. *A61B 3/102* (2013.01); *A61B 3/1225* (2013.01); *A61B 3/152* (2013.01)

(58) Field of Classification Search
USPC ................. 351/206, 205, 200, 209–211, 221, 222,351/243, 245, 246, 203, 204, 208, 216, 233,351/237, 244
See application file for complete search history.

(56) References Cited

U.S. PATENT DOCUMENTS 7,980,696 B1 * 7/2011 Taki .................. A61B 3/102
351/205
2007/0252951 A1   11/2007 Hammer et al.
(Continued)

FOREIGN PATENT DOCUMENTS

CN   1714740 A   1/2006
EP   1939580 A2  7/2008
(Continued)

*Primary Examiner* — Joseph P Martinez
*Assistant Examiner* — Brandi Thomas
(74) *Attorney, Agent, or Firm* — Canon USA Inc., IP Division (57) ABSTRACT

An ophthalmologic apparatus includes a tomographic image acquisition unit configured to acquire a tomographic image of a subject's eye based on a combined beam obtained by combining a return beam from the subject's eye, which is irradiated with a measuring beam, and a reference beam corresponding to the measuring beam, an optical path length difference changing unit configured to change an optical path length difference between the measuring beam and the reference beam, and a control unit configured to, in a case where relative positions of an optical system for irradiating the subject's eye with the measuring beam and an anterior segment of the subject's eye satisfy a predetermined condition based on an image of the anterior segment, control the optical path length difference changing unit so that the optical path length difference is within a predetermined range.

18 Claims, 10 Drawing Sheets

(56) References Cited

U.S. PATENT DOCUMENTS

2010/0033727 A1* 2/2010 Ko .................. A61B 3/102
356/451
2010/0110172 A1 5/2010 Satake

FOREIGN PATENT DOCUMENTS

| EP | 2184004 A1 | 5/2010 |
|---|---|---|
| JP | 2009291252 A | 12/2009 |
| JP | 2010181172 A | 8/2010 |
| JP | 2010197474 A | 9/2010 |
| JP | 2010256294 A | 11/2010 |
| WO | 2010/125746 A1 | 11/2010 |

* cited by examiner

OPHTHALMOLOGIC APPARATUS

TECHNICAL FIELD

The present invention relates to an ophthalmologic apparatus configured to capture an image of a subject's eye.

BACKGROUND ART

As an ophthalmologic apparatus, mainly an apparatus which acquires a tomographic image of the fundus of the subject's eye at a high resolution using an optical coherence tomography (OCT) and a scanning laser ophthalmoscope (SLO) are currently available.

Japanese Patent Application Laid-Open No. 2009-291252 discusses that an operator executes an alignment operation on the subject's eye using a joystick while observing the anterior segment of the subject's eye through a monitor and, when this alignment operation is completed, the SOL fundus image can be acquired. At this time, when the operator presses an auto-focus start switch, a focus lens arranged in an SLO optical system is moved based on the SLO fundus image. After the auto-focus lens arranged in the SLO optical system is moved, a focus lens arranged in the OCT optical system is also moved based on an SLO fundus image to execute a rough auto-focus for the OCT optical system. Further, after that, a reference mirror is moved based on the OCT tomographic image to automatically adjust a coherence gate, thereby achieving a precision auto-focus of the OCT optical system.

In addition, Japanese Patent Application Laid-Open No. 2010-181172 discusses that the operator operates a control lever to move a fundus camera unit to a subject side and then changes a display screen from an anterior segment image of the subject's eye to a fundus observation image prior to the alignment adjustment. At this time, after performing the change-over, an alignment light source is turned on to project an alignment bright point onto the subject's eye. After the alignment adjustment is completed, the focus adjustment is executed, and then, when it is determined that the alignment state is appropriate, the reference mirror is moved and the luminance value of the acquired OCT tomographic image is analyzed to automatically detect the OCT tomographic image. Japanese Patent Application Laid-Open No. 2010-181172 also discusses that the alignment adjustment may be executed manually or automatically.

When considering a physical burden on the subject, it is required to reduce a time taken until a main image capturing of the OCT is started. Because at this time, it is also desirable to reduce the burden on the operator, it is more useful to execute the alignment automatically than manually. However, when the display image is changed from the anterior segment image to the fundus observation image prior to the alignment adjustment, an alignment light source is required as well as the observation light source for acquiring the anterior segment image. Consequently, this not only leads to an enlargement in the size of the apparatus but also an increase of adjustment time due to a time taken until the alignment light source is stabilized after being turned on, thus increasing the burden on the subject.

SUMMARY OF THE INVENTION

According to an aspect of the present invention, an ophthalmologic apparatus includes tomographic image acquisition means configured to acquire a tomographic image of a subject's eye based on a combined beam obtained by combining a return beam from the subject's eye, which is irradiated with a measuring beam, and a reference beam corresponding to the measuring beam, optical path length difference changing means configured to change an optical path length difference between the measuring beam and the reference beam, and control means configured to, in a case where relative positions of an optical system for irradiating the subject's eye with the measuring beam and an anterior segment of the subject's eye satisfy a predetermined condition based on an image of the anterior segment, control the optical path length difference changing means so that the optical path length difference is within a predetermined range.

According to an exemplary embodiment of the present invention, when it is determined that the auto-alignment for the anterior segment is appropriate based on the image of the anterior segment of a subject's eye, the coherence gate position can be automatically adjusted. As a consequence, the adjustment time can be reduced, so that a time until a main image capturing of the OCT is started can be reduced and a burden on a subject can also be reduced.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

When it is determined that auto-alignment for an anterior segment is appropriate based on an image of the anterior segment of a subject's eye, an ophthalmologic apparatus according to an exemplary embodiment can automatically adjust a coherence gate position. As a consequence, the adjustment time can be reduced, so that a time taken until a main shooting operation of the OCT is started can be reduced and a burden on a subject can also be reduced.

The coherence gate mentioned here refers to a position corresponding to a reference beam optical path in a measuring beam optical path. Thus, by changing a difference in length of the optical path between the measuring beam and the reference beam with an optical path length difference changing unit, the position of the coherence gate can be changed. As the optical path length difference changing unit, a configuration which moves the position of the reference mirror along an optical axis and a configuration which moves the apparatus along the optical axis with respect to the subject's eye can be considered, and for example, a moving stage provided on the reference mirror or the apparatus is actually available.

Figure 5:
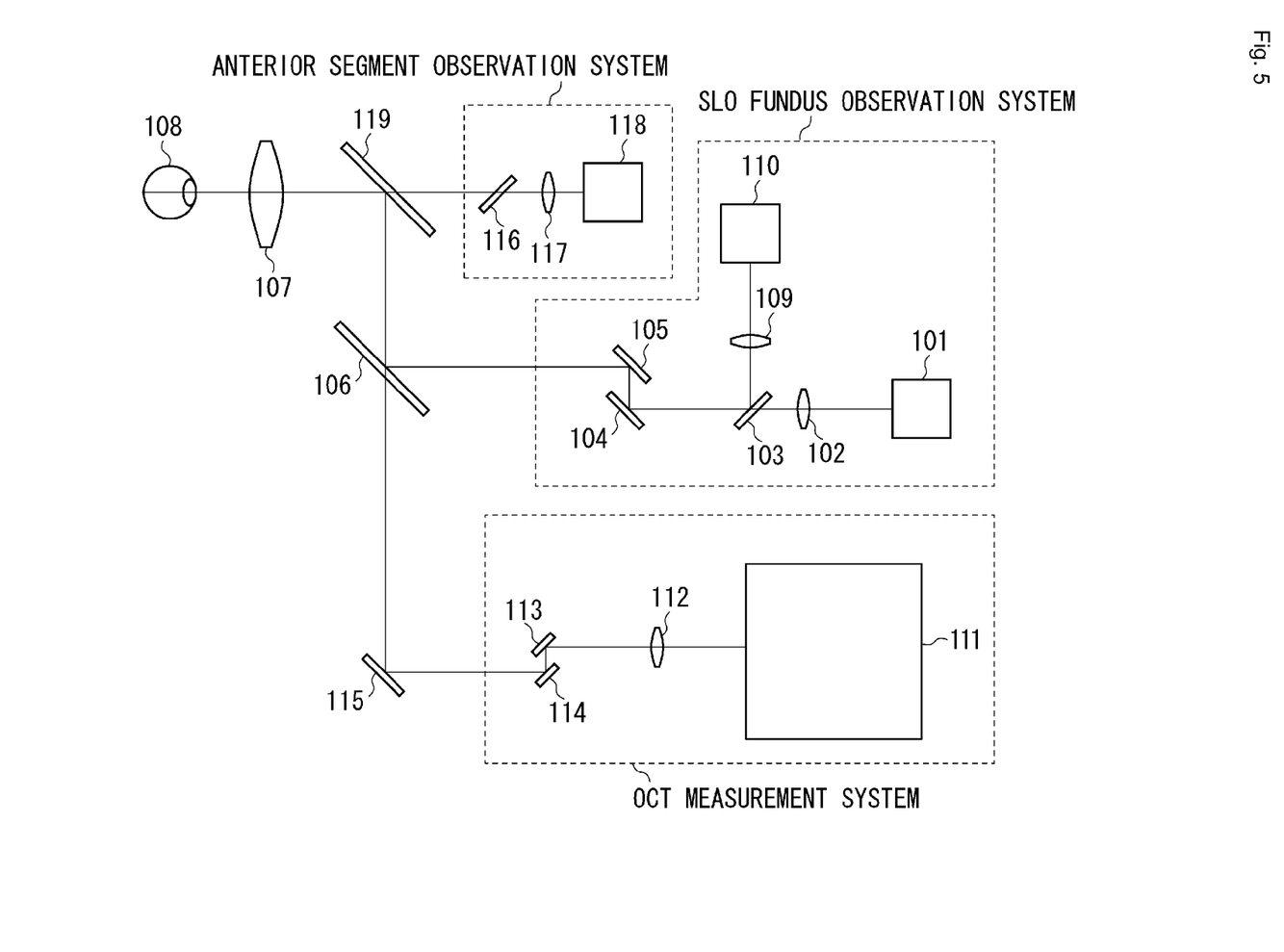
FIG. 5 is a schematic view illustrating a configuration of the ophthalmologic apparatus according to an exemplary embodiment of the present invention.
Figure 6:
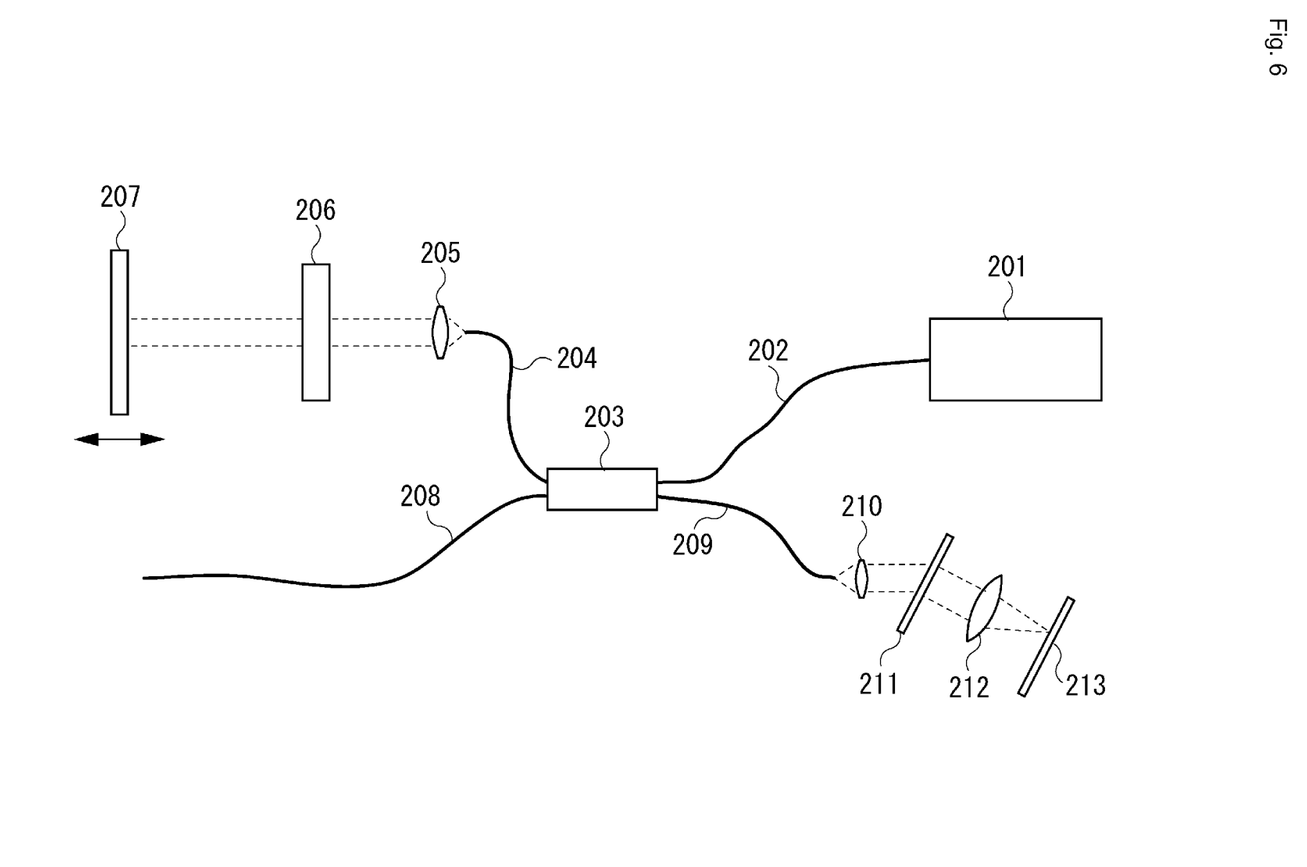
FIG. 6 is a schematic view illustrating a configuration of an OCT apparatus according to an exemplary embodiment of the present invention.

Next, each unit of the ophthalmologic apparatus according to the exemplary embodiment of the present invention will be described with reference to FIGS. 5 and 6. First, acquisition of the OCT tomographic image with an OCT measurement system will be described. A beam (low coherence beam) generated by a light source 201 for the optical coherence tomography (OCT) passes through a fiber 202 and is divided into a measuring beam, which is to be led to a fiber 208, and a reference beam, which is to be led to a fiber 204 and corresponds to the measuring beam. The measuring beam emitted from the end of the fiber 208 is collimated by a lens 112 provided outside an OCT unit 111, passes through XY scanners 113 and 114 (an example of a scanning unit for the OCT) for the OCT, is reflected by a mirror 115, is reflected by a beam splitter 119, and is projected onto a subject's eye 108 via an eyepiece lens 107. On the other hand, the reference beam emitted from the end of the fiber 204 is collimated by a lens 205, passes through a dispersion compensating glass 206, and is projected onto a reference mirror 207, which is movable in the optical axis direction. The dispersion compensating glass 206 is configured to compensate, with the reference beam, dispersion occurring in the measuring beam due to a component, for example, water, contained in the subject' eye 108. A return beam from the subject's eye (a beam dispersed and reflected by the subject's eye) and the reference beam reflected by the reference mirror 207 are combined together by a coupler 203 into a combined beam (called also an interference beam), which is then led to a fiber 209. The combined beam emitted from the end of the fiber 209 is collimated by a lens 210, is split by a diffraction grating 211 (an example of a light splitting unit for splitting a beam by each wavelength), and is projected onto a line sensor 213 (an example of an imaging unit for OCT) via a lens 213. Then, by Fourier-transforming an output from the line sensor 213, an OCT tomographic image can be obtained. Although the system illustrated in FIG. 6 is configured of a spectral-domain (SD)-OCT, the present invention may be applied to a swept-source (SS)-OCT. Further, although the system illustrated in FIG. 6 is a Michelson interferometer in which splitting of a beam and combination of beams are achieved with a common unit (the coupler 203), that system may be configured of a Mach-Zehnder interferometer.

Next, acquisition of an SLO fundus image with a fundus observation system will be described. A beam emitted from a light source 101 passes through a lens 102, a beam splitter 103, and XY scanners 104 and 105 (an example of a scanning unit for the SLO) for the SLO, is reflected by a beam splitter 106, is reflected by a beam splitter 119, and is then projected onto the subject's eye 108 via an eyepiece lens 107. A return beam from the subject's eye 108 is reflected by the beam splitter 103 and is then projected onto a dot sensor (an example of an imaging unit for the SLO) via a lens 109. An SLO fundus image can be acquired with an output from the dot sensor. By detecting a return beam from a subject's eye after infrared light or the like is projected onto the subject's eye without scanning the fundus of the subject's eye, a two-dimensional fundus image may be obtained based on a detection result of the return beam.

Acquisition of an anterior segment image with an anterior segment observation system will be described. The anterior segment of the subject's eye 108 is irradiated with a beam from a light source for the anterior segment (not illustrated). A return beam from the anterior segment passes through an image split prism 116, which will be described below, and is then projected onto a charge-coupled device (CCD) camera 118 (an example of an imaging unit for the anterior segment) via a lens 117. As a consequence, an anterior segment image can be obtained with an output of the CCD camera 118.

Figure 1:
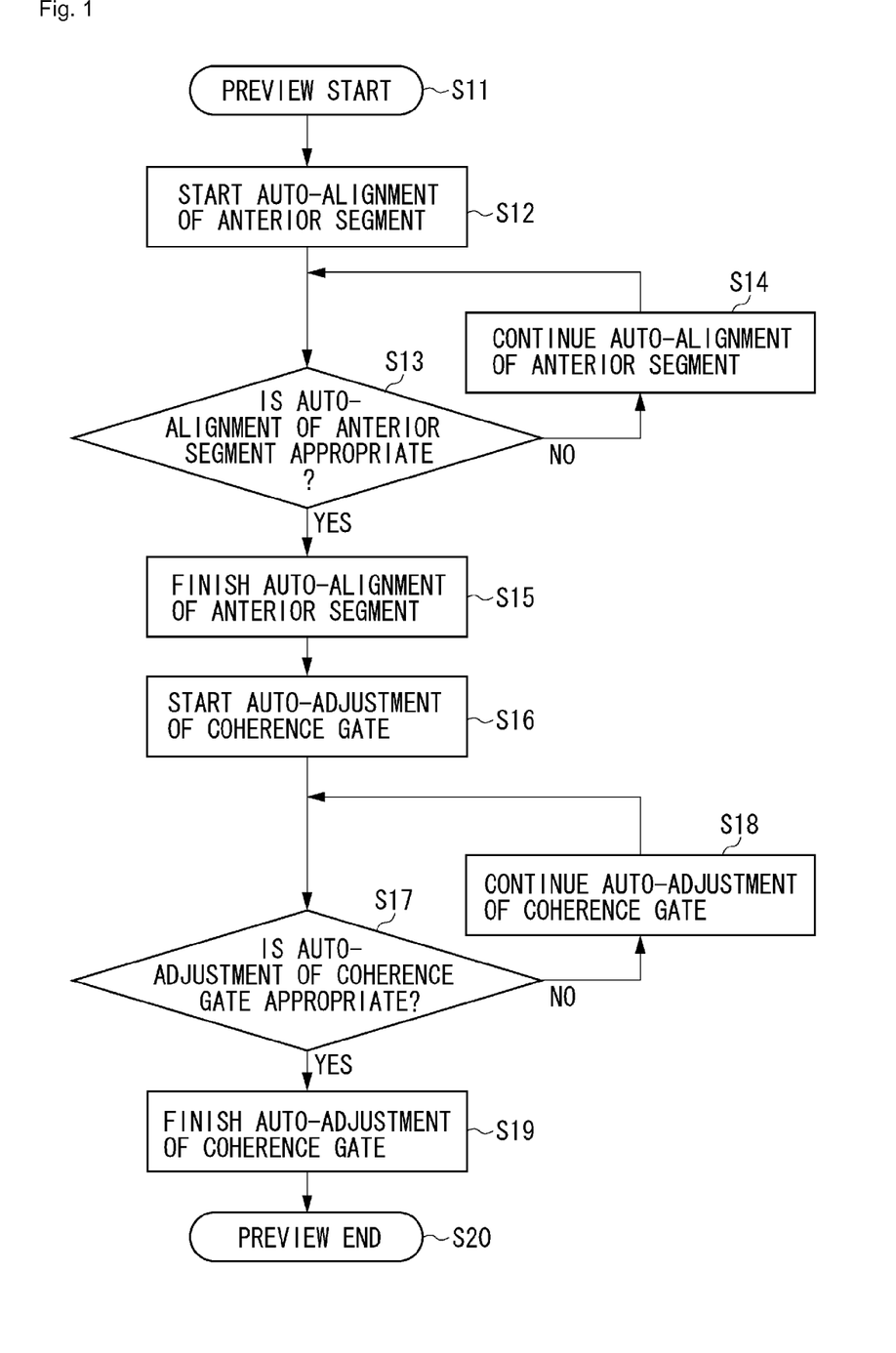
FIG. 1 is a flow chart illustrating respective steps to be executed by each unit of an ophthalmologic apparatus according to an exemplary embodiment of the present invention.

Respective steps to be executed by each unit of the ophthalmologic apparatus according to the present exemplary embodiment will be described with reference to the flow chart of FIG. 1.

In step S11, a control unit (not illustrated) starts a preview. The preview mentioned here refers to displaying the anterior segment image for positioning (alignment) of the apparatus and the subject's eye on a display unit or displaying an OCT tomographic image for a position adjustment of the coherence gate on the display unit prior to a main image capturing of the OCT. A tomographic image acquisition unit (not illustrated) acquires an OCT tomographic image of the subject's eye based on a combined beam obtained by combining a return beam from the subject's eye, which is irradiated with a measuring beam, and a reference beam corresponding to the measuring beam.

In step S12, the control unit (not illustrated) starts auto-alignment for the anterior segment. The auto-alignment for the anterior segment is achieved so that relative positions of the apparatus (an optical system which irradiates the subject's eye with the measuring beam) and the anterior segment satisfy a predetermined condition. More specifically, as changing of the relative positions, a configuration for moving the apparatus or a jaw mounting base for the subject's eye can be considered, and for example, a moving stage provided on the apparatus or the jaw mounting base is currently available.

In step S13, a determination unit (not illustrated) determines whether the auto-alignment for the anterior segment is appropriate. More specifically, the determination unit determines whether the aforementioned relative positions satisfy the predetermined condition. If the auto-alignment is appropriate, the processing proceeds to step S15, in which the auto-alignment for the anterior segment is finished. Otherwise, the processing proceeds to step S14, in which the auto-alignment for the anterior segment is continued until it becomes appropriate.

Figure 2A:
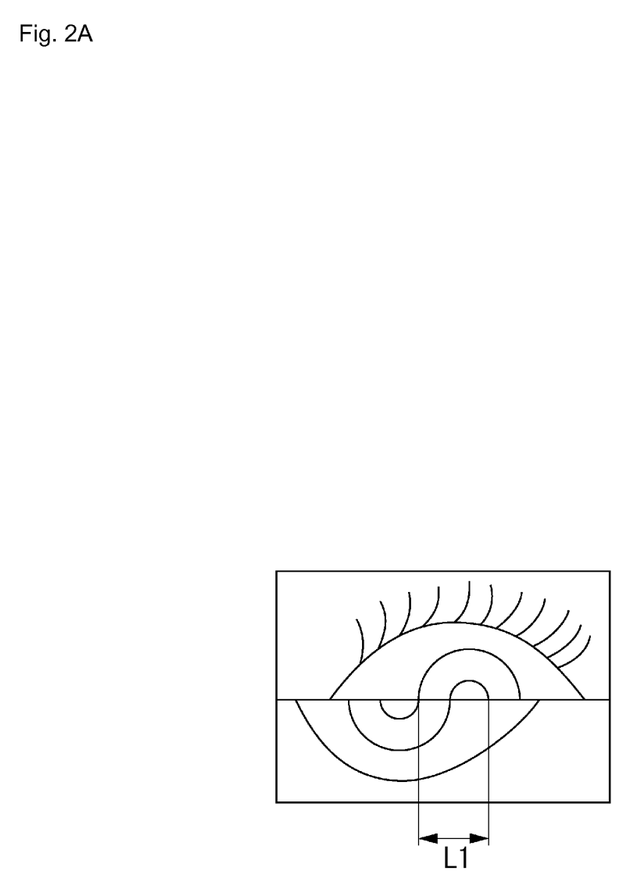
FIG. 2A is a schematic view illustrating an example of an alignment method according to an exemplary embodiment of the present invention.
Figure 2B:
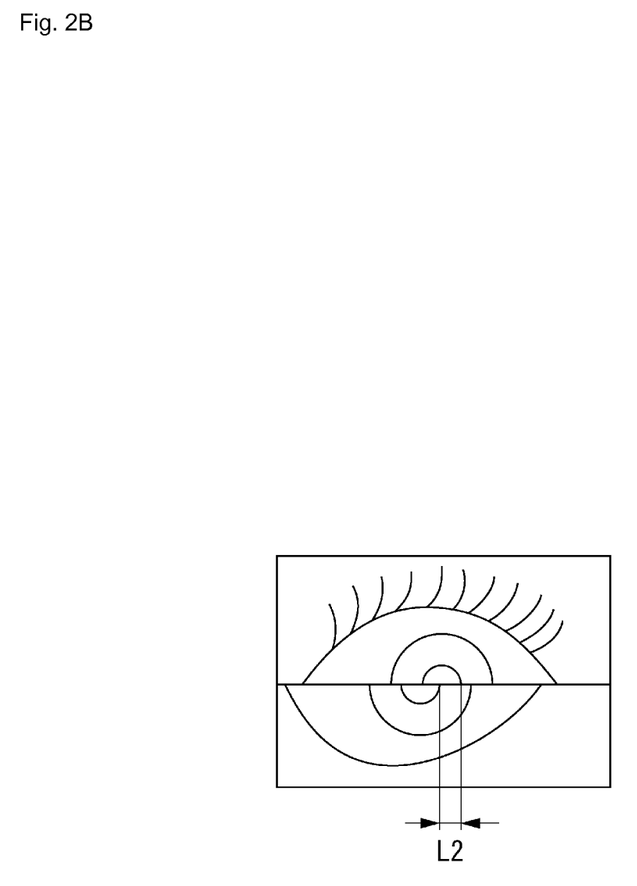
FIG. 2B is a schematic view illustrating the example of the alignment method according to the exemplary embodiment of the present invention.
Figure 2C:
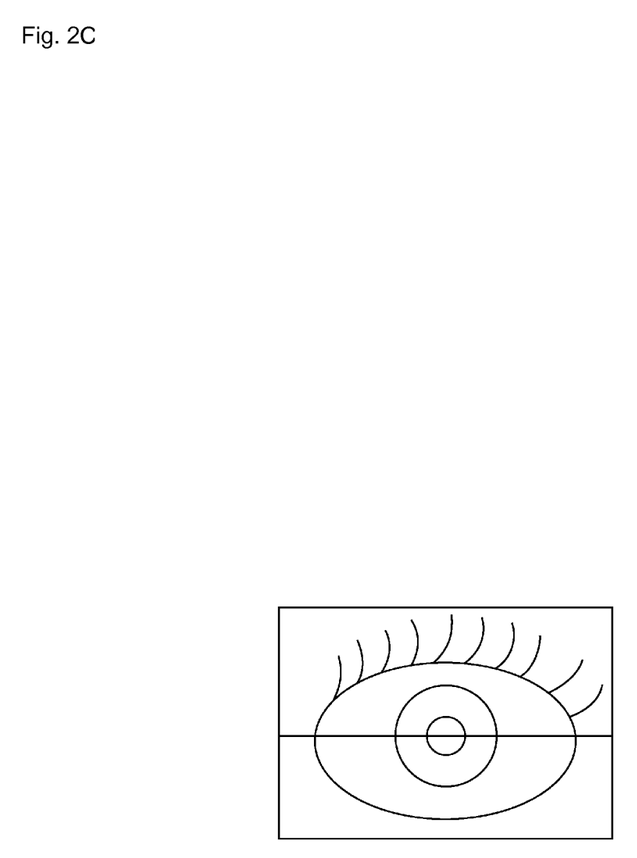
FIG. 2C is a schematic view illustrating the example of the alignment method according to the exemplary embodiment of the present invention.

A case where the relative positions satisfy the predetermined condition is, for example, a case where a distance between the anterior segment images obtained by splitting with the image split prism 116 is within a predetermined distance. FIGS. 2A, 2B, and 2C illustrate examples of the anterior segment images obtained by splitting. If the distance between the anterior segment images obtained by splitting is a length L1 which is larger than the predetermined distance L as illustrated in FIG. 2A, it is determined that the alignment is not appropriate. If as illustrated in FIG. 2B, the distance between the anterior segment images obtained by splitting is a length L2 which is smaller than the predetermined distance L, it is determined that the alignment is appropriate. If the distance between the anterior segment images obtained by splitting is substantially zero as illustrated in FIG. 2C, it means that the alignment is the best. Application of the image split prism 116 to a fundus camera is discussed in Japanese Patent Application Laid-Open No. 01-23134.

Figure 3A:
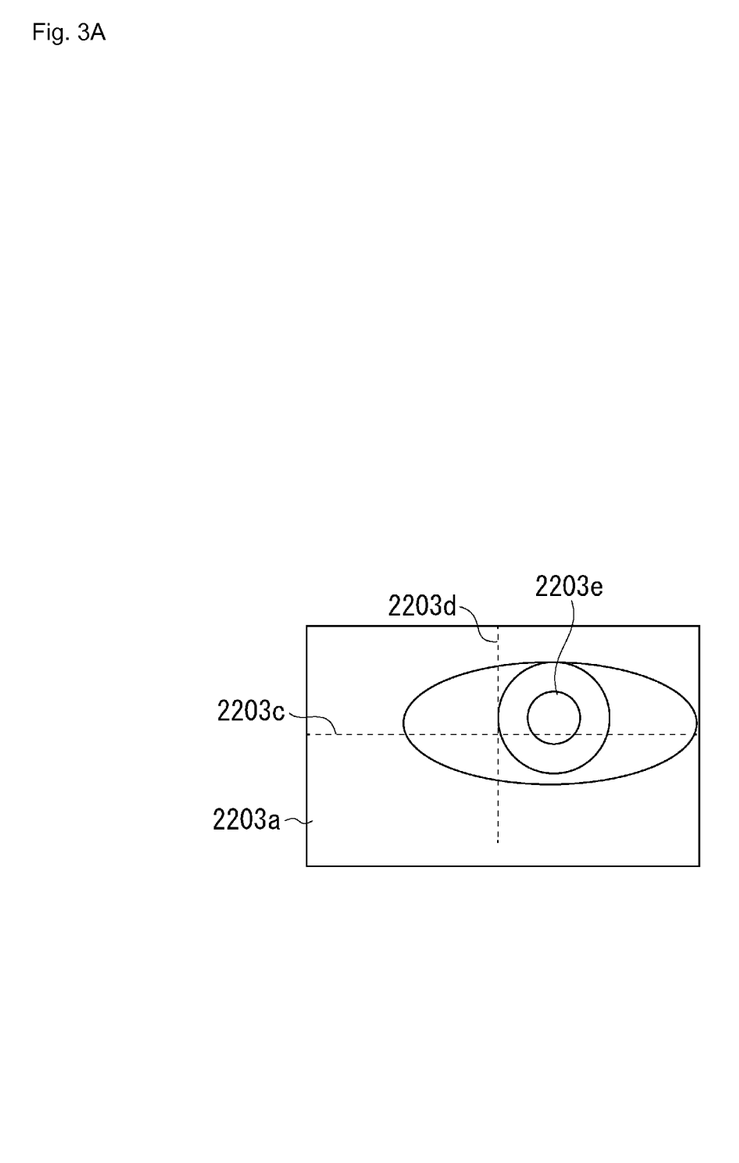
FIG. 3A is a schematic view illustrating an example of an alignment method according to an exemplary embodiment of the present invention.
Figure 3B:
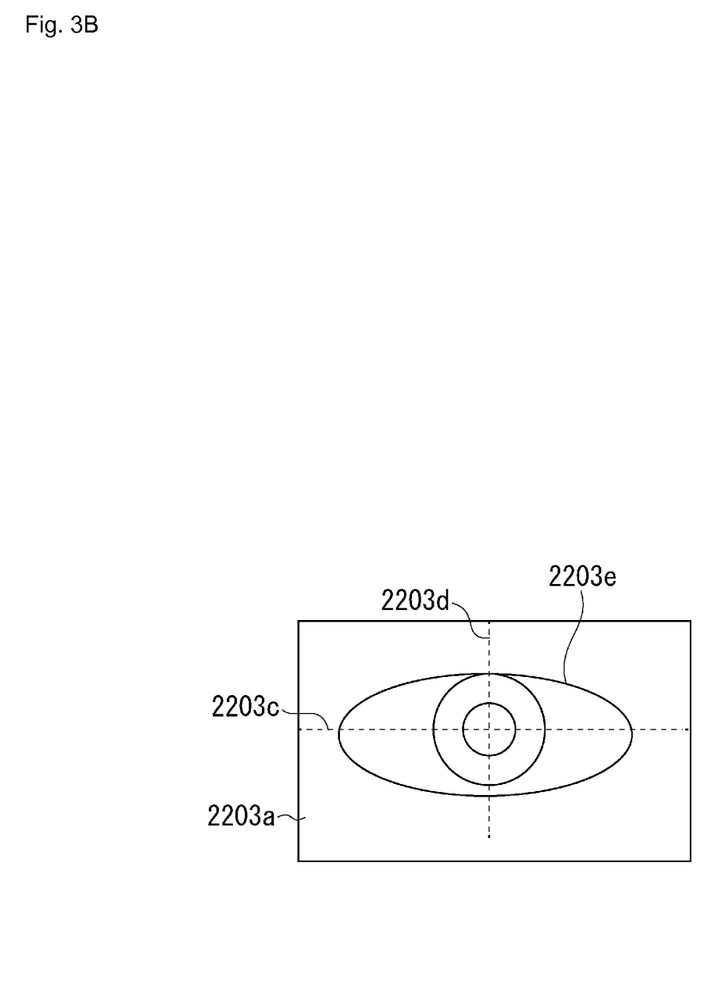
FIG. 3B is a schematic view illustrating the example of the alignment method according to the exemplary embodiment of the present invention.
Figure 3C:
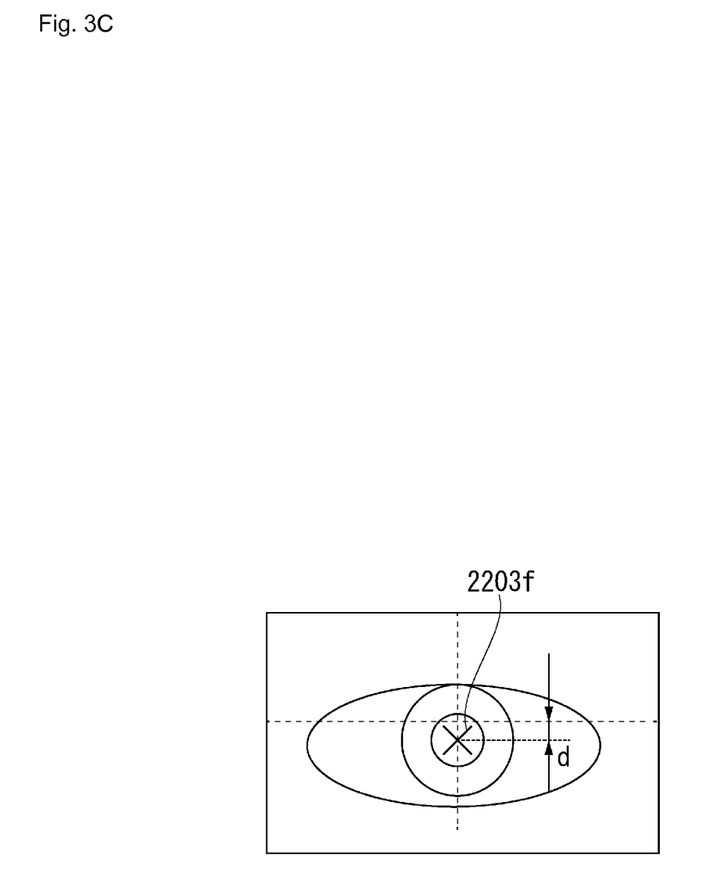
FIG. 3C is a schematic view illustrating the example of the alignment method according to the exemplary embodiment of the present invention.

A case where the aforementioned relative positions satisfy the predetermined condition is, for example, a case where the corneal luminescent spot of the anterior segment is located within a predetermined range. FIGS. 3A, 3B, and 3C illustrate examples of the anterior segment images. As illustrated in FIG. 3A, it is determined that there is a deflection in position in the X and Y directions between an image center which agrees with the optical axis of the measuring beam optical system of an optical head and the anterior segment image (the alignment is not appropriate). In this case, the control unit (not illustrated) moves the optical head so that the center of a pupil 2203e agrees with the image center as illustrated in FIG. 3B. However, they don't have to agree with each other completely, but even if the pupil 2203e is located at a position 2203f away from the image center by a predetermined distance d as illustrated in FIG. 3C, it can be determined that the alignment is appropriate. The anterior segment image is acquired by an anterior segment image acquisition unit constituted of the CCD camera 118 or the like. As regards deflection in position in the Z direction, it is permissible to use an anterior segment luminescent spot (not illustrated) based on a beam emitted from a light source for the anterior segment (not illustrated). In this case, the optical head can be moved and adjusted based on the size of the luminescent spot on an image of the anterior segment, and the optical head can be adjusted in the Z direction so that the size of the luminescent spot is minimized.

In step S16, the control unit (not illustrated) starts automatic adjustment of the coherence gate. More specifically, the optical path length difference changing unit is controlled so that the above-mentioned difference in optical path length is within the predetermined range. It is useful that the display control unit (not illustrated) displays the OCT tomographic image on a display unit (e.g., a monitor). In this case, a display position of the OCT tomographic image is determined based on the difference in optical path length (a position of the coherence gate). The case where the difference in optical path length is within the predetermined range refers to, for example, a case where a display position corresponding to the difference in optical path length is located at a predetermined display position or a case where a predetermined layer (e.g., a layer having a high intensity) of the OCT tomographic image is located at a predetermined display position.

In step S17, the determination unit (not illustrated) determines whether the automatic adjustment of the coherence gate is appropriate. More specifically, it is determined whether the difference in optical path length is within a predetermined range. If the automatic adjustment of the coherence gate is appropriate, the processing proceeds to step S19, in which the automatic adjustment of the coherence gate is finished. Further, the processing proceeds to step S20, in which the preview is finished. If the automatic adjustment is not appropriate, the processing proceeds to step S18, in which the automatic adjustment of the coherence gate is continued until it becomes appropriate.

After the preview is finished in step S20, the operator can capture an image of the subject's eye by pressing a shooting button (not illustrated). Alternatively, after the preview is finished in step S20, the subject's eye may be automatically shot. Because even if the alignment becomes appropriate, the subject's eye continues to move due to involuntary eye movement or the like, the alignment may be continued until the preview is finished in step S20 without finishing the alignment in step S15. In other words, the automatic adjustment of the coherence gate may be executed while continuing the alignment, or capturing of images may be executed while continuing the alignment. It is useful to configure the system so that the operator can select any one of an automatic mode which automatically executes adjustment of the alignment (positioning) and adjustment of the coherence gate position in sequence and a manual mode which executes these adjustments manually. When the automatic mode is selected, the manual mode (a mode in which an instruction unit can instruct changing) may be automatically selected after the automatic adjustment is finished. As a consequence, fine adjustment can be executed manually after rough adjustment is automatically executed, thus improving adjustment efficiency.

Next, another exemplary embodiment of the present invention will be described.

When the auto-alignment for the anterior segment is appropriate (when the aforementioned relative positions satisfy a predetermined condition), a focusing position can be changed by auto-focusing of a focusing position changing unit based on the intensity of a combined beam (or an SLO fundus image). Further, when the focusing position is changed, it is useful to control the optical path length difference changing unit so that the difference in optical path length is within a predetermined range. In other words, it is useful to execute the auto-focusing prior to the automatic adjustment of the coherence gate. As a consequence, the intensity during auto-focusing can be stabilized, thereby improving the precision of the auto-focusing.

When the focusing position is changed, it is useful to change the amount of light of the reference beam based on the intensity of the combined beam. As a light amount changing unit for changing the amount of light of the reference beam, for example, a neutral density (ND) filter (not illustrated) provided on a reference beam optical path is used. The ND filter is configured to be rotatable, so that the transmittance of the reference beam can be changed depending on a rotation angle. The intensity of the combined beam changes depending on the amount of light of the reference beam and the amount of light of the return beam. Thus, by attenuating any one or both of the reference beam and the return beam, the saturation of a detecting unit such as a line sensor can be suppressed. However, the intensity of the return beam is desirable to be as high as possible to prevent information from the subject's eye from being lost. If the amount of light of the reference beam is too large, the intensity of the combined beam may exceed the saturation level of each pixel of the detecting unit. For this reason, it is useful to attenuate the reference beam rather than the measuring beam. When the automatic adjustment of the coherence gate is executed under an excellent quality condition of the tomographic image, the adjustment precision is improved. Thus, it is useful to change the amount of light of the reference beam prior to the automatic adjustment of the coherence gate.

After the focusing position is changed, polarization of at least one of the reference beam and the measuring beam can be changed by a polarization changing unit (not illustrated) based on the intensity of the combined beam. Because a difference in polarization between the return beam from a subject's eye, which is irradiated with a measuring beam, and the reference beam causes a reduction in quality of the tomographic image, it is useful to automatically match polarization of the return beam with polarization of the reference beam. The polarization changing unit (not illustrated) is configured of a fiber loop of fibers provided on the reference beam optical path or the reference beam optical path. When the automatic adjustment of the coherence gate is executed under an excellent quality condition of the tomographic image, the adjustment precision is improved. Therefore, it is useful to change the polarization prior to the automatic adjustment of the coherence gate.

Figure 4:
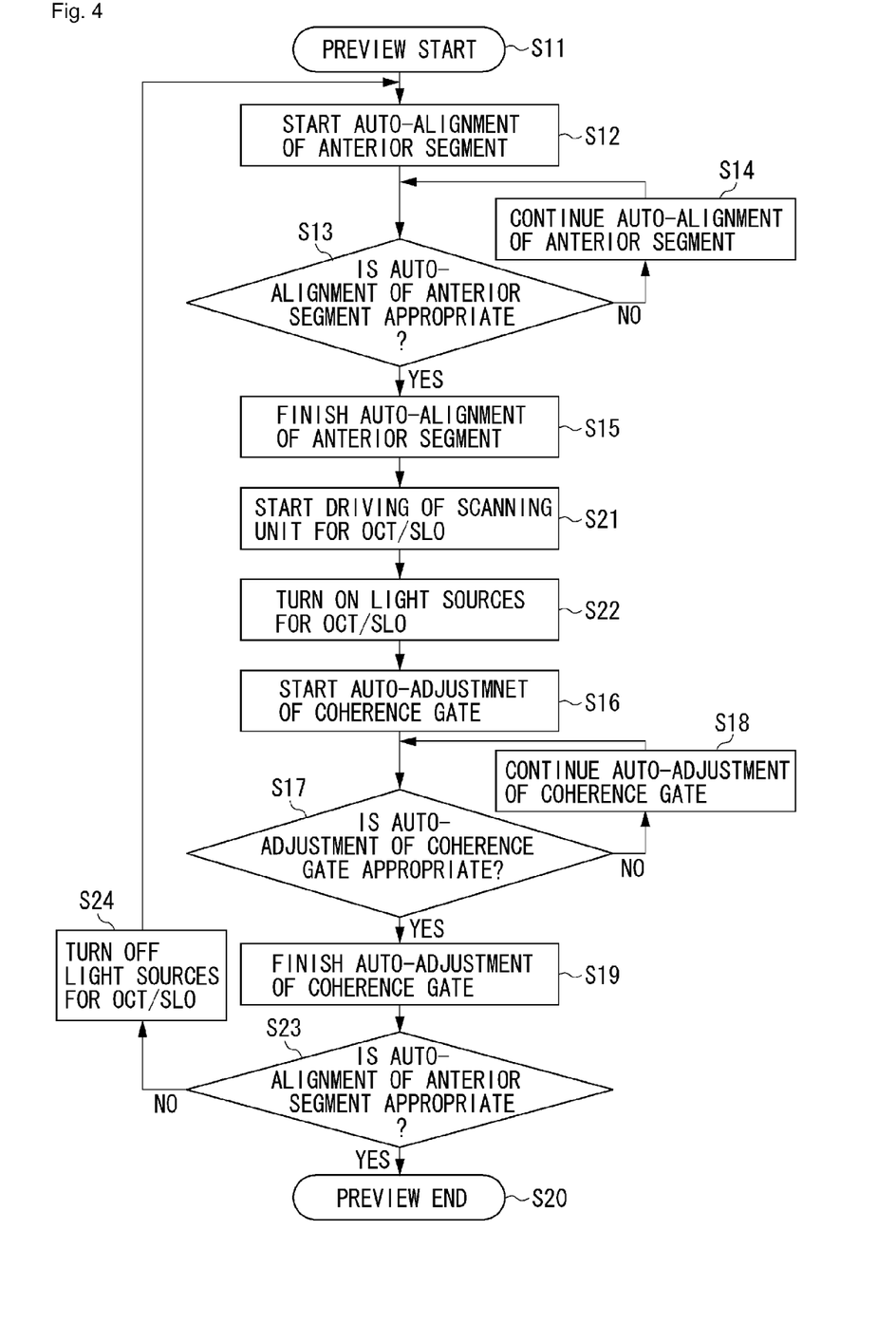
FIG. 4 is a flow chart illustrating steps to be executed by each unit of an ophthalmologic apparatus according to another exemplary embodiment of the present invention.

Respective steps to be executed by each unit of the ophthalmologic apparatus according to another exemplary embodiment will be described below with reference to the flow chart of FIG. 4. The same reference numerals as those in the flow chart of FIG. 1 indicate steps similar to the above-described respective steps, a description thereof is not repeated.

After the auto-alignment for the anterior segment is finished (when the aforementioned relative positions satisfy the predetermined condition) in step S15, the processing proceeds to step S21, in which a scanning unit (e.g., a galvanometer mirror for the OCT or a polygon mirror for the SLO) for scanning the fundus of the subject's eye with the measuring beam is driven. In step S22, the measuring beam is projected onto the subject's eye. Projection of the measuring beam onto the subject's eye can be performed by turning on the light source and removing a shielding unit (e.g., a shutter), which is provided removably with respect to an optical path of the light source or an optical path of the measuring beam, from the optical path. At this time, a timing on projecting the measuring beam onto the subject's eye is desirable to be in a period in which the alignment is finished while the scanning unit is being driven. This procedure is useful from the viewpoint of safety because the projection of an unnecessary beam onto the subject's eye during the alignment can be prevented. If prior to driving the scanning unit, the measuring beam is projected onto the subject's eye, a time in which the measuring beam is continuously projected onto a point of the subject's eye becomes long. Consequently, from the viewpoint of safety, it is useful that the scanning unit is driven before the measuring beam is projected onto the subject's eye. This configuration is applicable to a case of acquiring the SLO fundus image. Because control of the optical path length difference changing unit is executed based on the intensity (the intensity of the OCT tomographic image) of the combined beam, that control is executed when the measuring beam is projected onto the subject's eye. However, the alignment may be started with the scanning unit driven to project the measuring beam onto the subject's eye. In this case, because the light source can be stabilized during the alignment, a time until a main image capturing of the OCT is executed can be reduced.

After the automatic adjustment of the coherence gate is finished (when the difference in optical path length is within the predetermined range) in step S19, the processing proceeds to step S23, in which it is again determined whether the auto-alignment of the anterior segment is appropriate. If the auto-alignment of the anterior segment is appropriate, the processing proceeds to step S20, in which the preview is finished. If the auto-alignment of the anterior segment is not appropriate (if the aforementioned relative positions do not satisfy the predetermined condition), the processing proceeds to step S24, in which the measuring beam to be projected onto the subject's eye is reduced from the viewpoint of the safety of the subject's eye. For example, the light source is turned off or the shielding unit (e.g., a shutter), which is provided removably with respect to the optical path of the light source or the optical path of the measuring beam, is inserted into the optical path (the shutter is closed). From the viewpoint of safety, it is more useful to turn off the light source and insert the shielding unit into the optical path at the same time. This configuration is applicable to a case of acquiring the SLO fundus image.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-079361 filed Mar. 31, 2011, which is hereby incorporated by reference herein in its entirety.

The invention claimed is:

1. An ophthalmologic apparatus comprising:
a tomographic image acquisition unit configured to acquire a tomographic image of a subject's eye based on a combined beam obtained by combining a return beam from the subject's eye, which is irradiated with a measuring beam, and a reference beam corresponding to the measuring beam;
an optical path length difference changing unit configured to change an optical path length difference between the measuring beam and the reference beam;
an anterior segment image acquisition unit configured to acquire an image of an anterior segment of the subject's eye;
a determination unit configured to determine, based on the image of the anterior segment, whether relative positions of an optical system for irradiating the subject's eye with the measuring beam and the anterior segment satisfy a predetermined position range;
a scanning unit configured to scan a fundus of the subject's eye with the measuring beam; and
a control unit configured to change, when it is determined that the relative positions satisfy the predetermined position range, from a state that the subject's eye is not irradiated with the measuring beam to a state that the subject's eye is irradiated with the measuring beam while the scanning unit is driven, and to automatically control the optical path length difference changing unit so that the optical path length difference is within a predetermined length range in the state that the subject's eye is irradiated with the measuring beam.

2. The ophthalmologic apparatus according to claim 1, further comprising:

a display control unit configured to display, on a display unit, the tomographic image at a display position corresponding to the optical path length difference, wherein, in a case where the tomographic image is displayed at a predetermined display position, the optical path length difference is within the predetermined length range.

3. The ophthalmologic apparatus according to claim 1, further comprising:

a focusing position changing unit configured to, in a case where the relative positions satisfy the predetermined position range, change a focusing position of the measuring beam, wherein the control unit is configured to, in a case where the focusing position is changed, control the optical path length difference changing unit so that the optical path length difference is within the predetermined length range.

4. The ophthalmologic apparatus according to claim 3, further comprising:

a light amount changing unit configured to, in a case where the focusing position is changed, change an amount of light of the reference beam based on the intensity of the combined beam, wherein the control unit is configured to, when the amount of light of the reference beam is changed, control the optical path length difference changing unit so that the optical path length difference is within the predetermined length range.

5. The ophthalmologic apparatus according to claim 3, further comprising:

a polarization changing unit configured to, when the focusing position is changed, change polarization of at least one of the reference beam and the measuring beam based on the intensity of the combined beam, wherein the control unit is configured to, when the polarization is changed, control the optical path length difference changing unit so that the optical path length difference is within the predetermined length range.

6. The ophthalmologic apparatus according to claim 1, wherein, in a case where the relative positions do not satisfy the predetermined position range, the control unit is configured to reduce the measuring beam which is projected onto the subject's eye.

7. The ophthalmologic apparatus according to claim 6, wherein, in a case where the relative positions do not satisfy the predetermined position range, the control unit is configured to turn off a light source of the measuring beam.

8. The ophthalmologic apparatus according to claim 1, further comprising:

a light source; and a shielding unit configured to be removable with respect to an optical path of the light source and to shield against a beam from the light source, wherein, in a case where the relative positions satisfy the predetermined position range and the scanning unit is driven, the control unit is configured to remove the shielding unit from the optical path, and wherein, in a case where the relative positions do not satisfy the predetermined position range, the control unit is configured to insert the shielding unit into the optical path.

9. The ophthalmologic apparatus according to claim 1, wherein the anterior segment image acquisition unit is configured to acquire split images of the anterior segment, and wherein, in a case where a distance between the split images of the anterior segment is within a predetermined distance, the relative positions satisfy the predetermined position range.

10. The ophthalmologic apparatus according to claim 1, further comprising:

a light amount changing unit configure to, when the relative positions are detected as satisfying the predetermined position range, change an amount of light of the reference beam based on an intensity of the combined beam.

11. The ophthalmologic apparatus according to claim 1, further comprising:

a polarization changing unit configured to, when the relative positions are detected as satisfying the predetermined position range, change polarization of at least one of the reference beam and the measuring beam based on an intensity of the combined beam.

12. A driving method of an ophthalmologic apparatus comprising:

acquiring a tomographic image of a subject's eye based on a combined beam obtained by combining a return beam from the subject's eye, which is irradiated with a measuring beam, and a reference beam corresponding to the measuring beam;

acquiring an image of an anterior segment of the subject's eye;

determining, based on the image of the anterior segment, whether relative positions of an optical system for irradiating the subject's eye with the measuring beam and the anterior segment satisfy a predetermined position range;

changing, when it is determined that the relative positions satisfy the predetermined position range, from a state that the subject's eye is not irradiated with the measuring beam to a state that the subject's eye is irradiated with the measuring beam while a scanning unit is driven, the scanning unit scanning a fundus of the subject's eye with the measuring beam; and automatically controlling an optical path length difference changing means so that an optical path length difference is within a predetermined length range in the state that the subject's eye is irradiated with the measuring beam, the optical path length difference changing means changing the optical path length difference between the measuring beam and the reference beam.

13. A non-transitory computer-readable storage medium storing a program that causes a computer to execute the steps in the driving method according to claim 12.

14. An ophthalmologic apparatus comprising:

a tomographic image acquisition unit configured to acquire a tomographic image of a subject's eye based on a combined beam obtained by combining a return beam from the subject's eye, which is irradiated with a measuring beam, and a reference beam corresponding to the measuring beam;

an anterior segment image acquisition unit configured to acquire split images of an anterior segment of the subject's eye;

a determination unit configured to determine, in a case where a distance between the split images of the anterior segment is within a predetermined distance, whether relative positions of an optical system for irradiating the subject's eye with the measuring beam and the anterior segment satisfy a predetermined position range; and a control unit configured to automatically control, when it is determined that the relative positions satisfy the predetermined position range, the optical path length difference changing unit so that the optical path length difference is within a predetermined length range.

15. The ophthalmologic apparatus according to claim 14, wherein the anterior segment image acquisition unit is a charge-coupled device (CCD) camera configured to obtain the image of the anterior segment of the subject's eye before the tomographic image acquisition unit acquires the tomographic image of a subject's eye.

16. An ophthalmologic apparatus comprising:
  an image acquisition unit configured to acquire an image of a subject's eye based on a return beam from the subject's eye irradiated with a measuring beam;
  an focusing position changing unit configured to change a focusing position of the measuring beam;
  a scanning unit configured to scan a fundus of the subject's eye with the measuring beam; and
  a control unit configured to change a state that the subject's eye is not irradiated with the measuring beam to a state that the subject's eye is irradiated with the measuring beam while the scanning unit is driven and to automatically control the focusing position changing unit based on a return beam from the subject's eye irradiated with a measuring beam in the state that the subject's eye is irradiated with the measuring beam.

17. A driving method of an ophthalmologic apparatus comprising:
  acquiring an image of a subject's eye based on a return beam from the subject's eye irradiated with a measuring beam; and
  changing a state that the subject's eye is not irradiated with the measuring beam to a state that the subject's eye is irradiated with the measuring beam while a scanning unit is driven, the scanning unit scanning a fundus of the subject's eye with the measuring beam; and
  automatically controlling a focusing position changing unit based on a return beam from the subject's eye irradiated with a measuring beam in the state that the subject's eye is irradiated with the measuring beam, the focusing position changing unit changing a focusing position of the measuring beam.

18. A non-transitory computer-readable storage medium storing a program that causes a computer to execute the steps in the driving method according to claim 17.

* * * * *